United States Patent [19]

Lee, Jr. et al.

[11] 4,032,504

[45] June 28, 1977

[54] X-RAY OPAQUE FILLER USEFUL IN DENTAL AND MEDICAL RESTORATIVE COMPOUNDS

[75] Inventors: Henry L. Lee, Jr., Pasadena; Jan A. Orlowski, Altadena, both of Calif.

[73] Assignee: Lee Pharmaceuticals, South El Monte, Calif.

[22] Filed: Dec. 19, 1974

[21] Appl. No.: 534,374

Related U.S. Application Data

[63] Continuation of Ser. No. 401,810, Sept. 28, 1973, abandoned.

[52] U.S. Cl. ............................... 260/42.18; 106/35; 106/288 B
[51] Int. Cl.² ...................... C09K 3/00; C08K 7/14
[58] Field of Search ................... 260/998.11, 42.18; 106/35, 308, 288

[56] References Cited

UNITED STATES PATENTS

| 1,408,960 | 3/1922 | Schiff | 106/35 |
|---|---|---|---|
| 3,539,533 | 11/1970 | Lee | 260/47 |
| 3,751,399 | 8/1973 | Lee et al. | 106/35 |

OTHER PUBLICATIONS

J. Dent. Res. Jan–Feb. 1969, vol. 48, No. 1, pp. 79–82 "X-Ray Opaque Reinforcing Filters for Composite Materials" Bowen et al.

*Primary Examiner*—Theodore Morris
*Attorney, Agent, or Firm*—Irons & Sears

[57] ABSTRACT

A novel X-ray opaque filler for synthetic resinous compositions including dental and medical restorative materials is disclosed.

10 Claims, 3 Drawing Figures

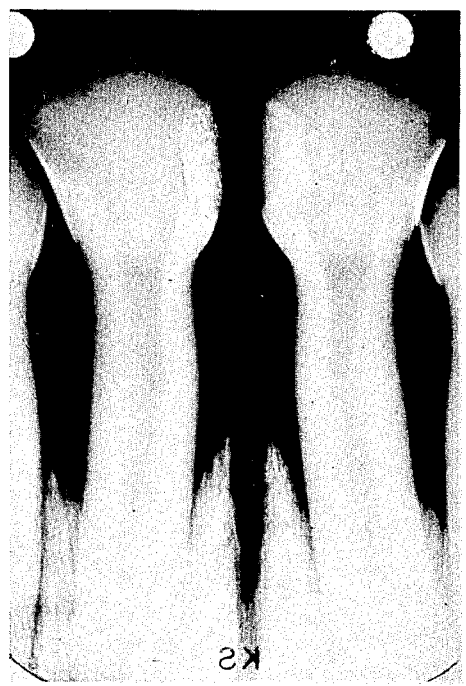
FIG. A
FIG. B

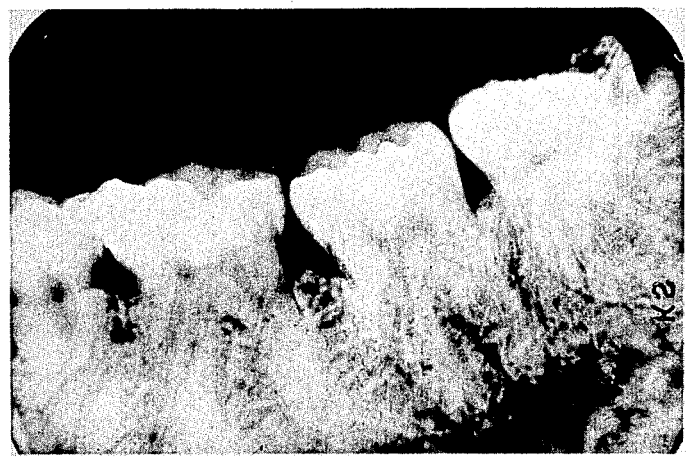
FIG. C

X-RAY OPAQUE FILLER USEFUL IN DENTAL AND MEDICAL RESTORATIVE COMPOUNDS

BENEFIT OF PRIOR APPLICATION

This application is a continuation of application Ser. No. 401,810 filed Sept. 28, 1973 now abandoned.

BACKGROUND OF THE INVENTION

Description of the Prior Art

In the manufacture of plastic filling materials for teeth it is common practice to utilize powdered glass or quartz as an inert filler for the resin binders utilized.

The refractive index of fillers and the refractive index of cured conventional acrylic binders used in dental and medical restorative compositions are similar and ordinarily on the order of 1.45 to 1.56. Upon placement of such silica glass-filled plastic restorative and cure of the acrylic resin binder, a translucent restoration is achieved. Such restorations reflect color from the adjacent tooth surfaces and blend nicely with the shade of the restored tooth particularly when the restoration is not too large.

Conventional silica glass-containing restorations lack X-ray opacity requisite to permit the dentist to distinguish the restorative material from decalcified tooth structure such as is present in a carious lesion and to detect subgingival overhangs. To provide X-ray opacity, barium glass is sometimes utilized in lieu of conventional glass in such restorative compositions. Barium glass having a refractive index in the desired range of 1.5 to 1.6 is, however, characterized by limited X-ray opacity and is often unduly soft and soluble in strong acids, hence plastic restorations utilizing such barium glass do not reliably afford a long service life and are of relatively low compressive strength. For example, conventional acrylic restorative compositions filled with odinary silica or borosilicate glass may achieve a compressive strength of about 45,000 psi whereas barium glass restorative compositions containing barium of refractive index in the range of about 1.5 to 1.6 seldom if ever achieve compressive strength values in excess of 30,000 psi.

SUMMARY OF THE INVENTION

This invention provides a filler composition for synthetic resinous compositions including dental and medical restorative materials which is effectivey X-ray opaque characterized by a refractive index which approximates the refractive index of the cured resin binder and which provides cured compositions of acceptable acid resistance and physical properties including compressive strength.

The invention specifically entails the practical application to the art of preparing composite dental and medical restorative compositions of three interrelated discoveries It has been demonstrated that effective X-ray opacity is achieved when a minor proportion, on the order of 10 to 35% by weight, of the filler material is of higher refractive index than the balance of the composition and hence that it is unnecessary for all of the filler in the restorative composition to match closely the refractive index of the cured binder. For example, a filler comprising as much as 25 to 35% of barium glass of higher refractive index than the binder in the range of from about 1.7 to about 2.0, with the balance conventional or Borosilicate glass of refractive index approximating that of the cured binder not only provides effective X-ray opacity but also demonstrates a translucency approximating the pearlescent translucency of natural teeth. Such minor proportions of higher refractive index barium glass have minimal effect on the mechanical properties and acid resistance of the cured restorative. Thus cured X-ray opaque restorative compositions having a compressive strength in the range of 40,000 to 45,000 psi are readily achieved.

The cured X-ray opaque restorative compositions of this invention in which strongly X-ray opaque materials are distributed in a non-X-ray-opaque milieu provide X-ray pictures which distinguish restorations from normal tooth structure and from decay more effectively than conventional X-ray opaque materials in which the filler is substantialy entirely barium glass. The particles of high barium glass content stand out among the balance of the filler particles under X-rays to provide contrast which is at least as good as that achieved when a filler consisting entirely of X-ray opaque barium glass of refractive index about 1.5 to about 1.6 is utilized. The cured restorative compositions of the invention actually provide a greater contrast on X-ray film than would be expected upon the basis of the relative proportion of high refractive index barium glass present apparently because the X-rays are reflected or deflected markedly by the localized concentration of barium-containing material.

The result is that an X-ray picture of a restoration of this invention is not uniformly gray but is sparkly and grainy in appearance. Uniquely different shades are produced by the X-ray opaque restorative, the tooth structure and solid metal fillings. Thus the invention results in X-ray pictures which are more easily interpreted than X-ray pictures of restorations made with prior art materials, and does so without the sacrifice in acid resistance and compressive strength which results when lower refractive index barium glass alone is used as a fillter The difference between the appearance of X-ray pictures of restorations made from the composition of the invention and X-ray pictures of restorations made from filled acrylic resin type restorative compositions containing no X-ray opaque material can readily be seen by comparing FIG. A, a reproduction of an X-ray picture of a tooth containing a restoration of the composition of the invention, with FIG. B, a reproduction of an X-ray picture of a tooth structure containing a restoration made from an acrylic resin type composition containing no barium glass or other X-ray opaque material. FIG. C is a reproduction of an X-ray picture of tooth structure containing a restoration prepared from metal amalgam and it will readily be seen that it, too, is easily distinguished from FIG. A.

Fillers of this invention appropriately contain up to about 30% by weight, preferably from about 10 to about 30% by weight, of a barium glass having a high refractive index of from about 1.7 to about 2.0 with the balance formed from essentially X-ray transparent filler materials such as silica, quartz, glass, micro fibrous refractory salts such as calcium silicate or mixtures thereof, or any other inert filler material. Borosilicate glass is preferred. Both the high refractive index barium glass and the balance of the filler composition are preferably of a particle size of from about 0.5 to about 50 microns with an average particle size of from about 2 to about 15 microns.

The component of the filler composition other than the barium glass of refractive index from about 1.7 to about 2.0 should closely approximate the refractive index of the cured resin binder. In general, the refractive index of the cured resin should match that of the essentially X-ray transparent filler material within about 0.005 refractive index units but differences of 0.01 and even greater differences up to about 0.1 are acceptable in some instances. Thus, for example, where the refractive index of the cured resin binder is in the order of 1.53, the refractive index of the X-ray transparent filler material should desirably be not less than about 1.52 nor more than about 1.54. It should be recognized, however, that there are some tooth shades with which an X-ray transparent filler material with a refractive index value in the range of from about 1.43 to about 1.63 could work quite adequately with a cured resin binder having a refractive index in the order of about 1.53. In addition, it should be recognized that finer particle size materials must match more closely insofar as refractive index values are concerned than larger particles. The smaller the particle, the more interfaces it provides for refraction in the context of the entire composition with the result that small differences in refractive index are effectively multiplied and tend to be more descernible to the naked eye than in the case of larger particles of the same composition.

The term "refractive index" as applied to powdered specimens throughout this specification is intended to refer to refractive index as measured by a conventional test which involves immersing a measured quantity of the powder in a series of mixed liquids, each of known refractive index, and determining the time at which the powder disappears, whereupon the refractive indices of the resultant solutions are measured and appropriate calculations are made.

Any synthetic resin binder useful in dental and medical composite restorative compositions can be utilized with the fillers of this invention. Presently available materials are primarily acrylic resins. Typical commercial products include the quartz filled composite dental restorative composition of the aliphatic diacrylate/aromatic diacrylate type sold by Johnson & Johnson, Inc. under the trademark name "Adaptic", the composite restorative comprising silica filled aromatic/aliphatic diacrylate sold by Lee Pharmaceuticals under the trade name "Prestige", the unfilled aromatic/aliphatic diacrylate cured by ultraviolet light sold under the trade name "Nuva Seal" by L. D. Caulk Co., the commercial produce "Concise" sold by Minnesota Mining & Mfg. Co. which is essentially a quartz filled product of the aromatic/aliphatic diacrylate type. Typical commercial resins are disclosed, inter alia, in Dennison et al, "Physical Properties and Finished Surface Texture of Composite Restorative Resins", Journal of the American Dental Association, Vol 85, pp. 101-108 (1972); Hollenback, G. M., "A Further Report on the Physical Properties of the Five Composite Resins, Part II", Journal of Alabama Dental Associaton, Vo;. 55, pp. 17-23 (1971); Peterson et al, "A Comparison of the Physical Properties of Four Restorative Resins", Journal of the American Dental Association, Vol. 73, pp. 1324-1336 (1966); and in United States patents Bowen U.S. Pat. Nos. 3,066,112 and 3,179,623, Lee et al, 3,539,533 and 3,751,399 and Stoffey and Lee 3,730,947.

In dental and medical restorative compositions the fillers of this invention appropriately comprise from about 40% to about 90%, preferably about 60% to about 85% of the total weight of the cured restorative material.

While the X-ray opaque filler composition of the invention has been described with particular reference to dental and medical restorative compositions, it is equally useful to provide X-ray opacity in any filled synthetic or natural resin product. Thus articles formulated from polyethylene, polycarbonate, polypropylene or any other synthetic resin may properly utilize the fillers of this invention to obtain X-ray opacity.

DESCRIPTION OF THE PREFERRED EMBODIMENTS OF THE INVENTION

The following description of the preferred embodiments of the invention are representative only. Other embodiments of the invention within the scope of the claims will be readily apparent to a person skilled in the art.

EXAMPLE I

The X-ray opaque filler composition utilized in this example was a mixture of 60 parts by weight of X-ray transparent Borosilicate glass having a refractive index of 1.47 and 20 parts by weight of X-ray opaque barium glass having a refractive index of 1.93.

The particles of Borosiliate and Barium glass were reduced in size by high speed direct impact in a stream of air, of the particles upon one another and upon a nonmetallic surface utilized to avoid metal contamination. The particle size of the Borosilicate glass and of the barium glass utilized was from about 0.5 to about 30 microns, the average particle size being about 2 microns. The Borosilicate glass was Corning 7740 purchased from Corning Glass Works. The barium glass was Potters H-002 purchased from Potter Industries, Carstadt, N. J.

80 parts dry weight of opaque filler composition was combined with a polymerizable monomer composition composed of 1 parts by weight of diglycidyl ether of bis phenol-A dimethacrylate and 10 parts by weight of triethyleneglycol dimethacrylate catalyzed with 0.4 parts by weight of benzoyl peroxide and 0.2 parts by weight of N,N-dimethyl-para-toluidine.

The cured restorative composition was characterized by the following physical properties:

| | |
|---|---|
| Compressive strength | 44,000 psi |
| Diametral tensile strength | 7,500 psi |
| Hardness, Rockwell H | 114 |
| Translucency quotient ($C_{70}$) | 0.6 |

The test methods utilized were essentially the methods disclosed in the copending application Ser. No. 386,417 of Lee and Orlowski filed Aug. 7, 1973.

In addition, a disk of a specimen 1 inch in diameter and ⅛ inch thick prepared from the composition of the invention was tested for acid insolubility against specimens of the same size and dimensions prepared from the commerical products Concise and Adaptic cured in accordance with the directions for optimum cure given by the manufacturers in the product packages as sold. Each of the disk specimens of the respective materials was then extracted for 120 hours in a 5% solution of aqueous acetic acid. The composition of this invention exhibited a weight loss of 0.5% at the end of the test.

The Concise disk showed a weight loss of 0.58% and the Adaptic showed a weight loss of 1.41%.

The composition of this example was tested in vitro as a filling material for bovine teeth and was found to provide excellent X-ray contrast to the tooth structure.

EXAMPLE II

A composition having the following formulation was prepared and cured:

| | |
|---|---|
| Diglycidyl ether of bis phenol-A dimethacrylate | 16.0 parts by weight |
| Triethyleneglycol dimethacrylate | 8.0 parts by weight |
| Benzoyl peroxide | 0.3 parts by weight |
| N,N-bis (2-hydroxyethyl) toluidine | 0.4 parts by weight |
| Amorphous silica (refractive index 1.55; particle size range 0.5 to about 30 microns; average particle size about 2 microns) | 56.0 parts by weight |
| Barium glass (refractive index 1.85; particle size essentially the same as the silica) | 20.0 parts by weight |

When cured and tested similarly to the product of Example I, the following properties were determined:

| | |
|---|---|
| Compressive strength | 48,000 psi |
| Diametral tensile strength | 7,500 psi |
| Hardness, Rockwell H | 113 |
| Translucency quotient ($C_{70}$) | 0.52 |

EXAMPLE III

Utilizing the same formulations as Example II and substituting the same number of parts by weight of quartz of the same particle size and refractive index for the amorphous silica, a composition was obtained which had the following properties when tested in the same manner as the compositions of Examples I and II:

| | |
|---|---|
| Compressive strength | 35,000 psi |
| Diametral tensile strength | 6,900 psi |
| Hardness, Rockwell H | 114 |
| Translucency quotient ($C_{70}$) | 0.48 |

In comparison to the properties obtained with the compositions of Examples I, II and III, specimens of the same size and shape made from commercial Adaptic and commercial Concise and cured in accordance with the manufacturers' directions for attaining optimum cure were tested for the same properties according to the same methods. The results for Adaptic were as follows:

| | |
|---|---|
| Compressive strength | 34,000 psi |
| Diametral tensile strength | 6,500 psi |
| Hardness, Rockwell H | 103 |
| Translucency quotient ($C_{70}$) | 0.45 |

The results for Concise were as follows:

| | |
|---|---|
| Compressive strength | 29,350 psi |
| Diametral tensile strength | 5,910 psi |
| Hardness, Rockwell H | 101 |
| Translucency quotient ($C_{70}$) | 0.66 |

In all cases, both in vitro and in vivo testing has demonstrated significantly improved X-ray opacity characteristics relative to restorative compositions prepared from Adaptic or Concise.

What is claimed is:

1. An X-ray opaque filler for synthetic resin compositions comprising from about 5% to about 35% by weight of particulate barium glass having a refractive index of from about 1.7 to about 2.0 and from about 95 to about 65% by weight of an X-ray transparent particulate filler material having a refractive index which closely approximates the refractive index of the synthetic resin composition to be filled.

2. A composition according to claim 1 in which the filler material is selected from the group consisting of silica, quartz, silica glass and micro fibrous refractory salts.

3. A composition according to claim 1 in which the particle size of the filler composition is in the range of from about 0.5 to about 50 microns and the average particle size is from about 2 to about 15 microns.

4. A filler according to claim 3 in which the particle size range is from about 0.5 to about 30 microns and the average particle size is about 2 microns.

5. A composition of matter comprising from about 10% to about 60% by weight of a polymerizable monomer and from about 90% to about 40% by weight of a filler plus minor amounts in the order of about 2% or less of conventional curing ingredients, said filler comprising a combination of from about 90% to about 65% by weight of the filler of the powdered inert X-ray transparent filler having a refractive index which closely approximates that of the cured monomer and from about 10% to about 35% by weight of the filler of a powdered X-ray opaque barium glass having a refractive index in the range of from about 1.7 to about 2.0.

6. A composition of matter according to claim 5 in which the barium glass has a refractive index of about 1.9, the particle size of the filler is from about 0.5 to about 30 microns, the average particle size being about 2 microns, and the polymerizable monomer is a mixture of equal parts by weight of diglycidyl ether of bis phenol-A dimethacrylate and triethyleneglycol dimethacrylate and the powdered inert X-ray transparent filler is a Borosilicate glass.

7. A composition according to claim 6 in which the powdered glass and the cured monomer have a refractive index in the range of from about 1.4 to about 1.6.

8. A composition according to claim 5 which is useful as a dental restorative composition and which comprises as polymerizable monomer about 10 parts by weight of diglycidyl ether of bis phenol-A dimethacrylate, about 10 parts by weight of triethyleneglycol dimethacrylate, about 60 parts by weight of powdered Borosilicate glass having a refractive index of about 1.47, about 20 parts by weight of powdered barium glass having a refractive index of about 1.9, the Borosilicate glass and barium glass each having a particle size in the range of from about 0.5 to about 30 microns and an average particle size of about 2 microns.

9. A composition according to claim 5 useful as a dental restorative composition in which the polymerizable monomer comprises about 16 parts by weight of diglycidyl ether of bis phenol-A dimethacrylate, about 8 parts by weight of triethyleneglycol dimethacrylate and the filler comprising about 56 parts by weight of amorphous silica having a refractive index of about 1.55 and about 20 parts by weight of barium glass having a refractive index of about 1.85, the particle size of the filler being in the range of from about 0.5 to about 30 microns and the average particle size being about 2 microns.

10. A composition according to claim 9 in which the filler includes, in lieu of about 56 parts by weight of amorphous silica, about 56 parts by weight of powdered quartz having a refractive index of about 1.55.

* * * * *